United States Patent [19]

Stewart

[11] 4,152,598
[45] May 1, 1979

[54] LUBRICANT DISTRIBUTION DETERMINATION BY NEUTRON RADIOGRAPHY

[75] Inventor: Peter A. E. Stewart, Bristol, England

[73] Assignee: Rolls-Royce (1971) Limited, Bristol, England

[21] Appl. No.: 752,520

[22] Filed: Dec. 20, 1976

[30] Foreign Application Priority Data

Dec. 23, 1975 [GB] United Kingdom .............. 52592/75

[51] Int. Cl.$^2$ ................................................ G01T 3/00
[52] U.S. Cl. ..................................... 250/391; 250/392
[58] Field of Search ......................... 250/390, 391, 392

[56] References Cited

U.S. PATENT DOCUMENTS 3,359,419  12/1967  Kastner et al. .................. 250/390 X

OTHER PUBLICATIONS

Nuclear Instruments and Methods, vol. 92, No. 4, pp. 613-617 (1971), Use of a 10" n/sec. Neutron Generator for Neutron Radiography, by A. R. Spowart, N. Holland Pub. Co.

*Primary Examiner*—Alfred E. Smith
*Assistant Examiner*—Janice A. Howell
*Attorney, Agent, or Firm*—Stevens, Davis, Miller & Mosher

[57] ABSTRACT

Cold neutron radiation of energy less that 0.025 eV having a flux greater than $1 \times 10^3$ neutrons/square centimeter/second is used to diagnose temporal information about the spatial distribution of hydrocarbon fuel and lubrication oils in internal combustion engines, gas turbine engines and fuel systems.

Images of the movement of fuel or oil are recorded by directing a beam of neutrons through an engine and using an image intensifier responsive to low light levels to intensify an image formed by neutrons which have been directed through the engine onto a fluorescent screen. The output image from the intensifier is recorded by a video or cine camera.

10 Claims, 7 Drawing Figures

LUBRICANT DISTRIBUTION DETERMINATION BY NEUTRON RADIOGRAPHY

The present invention relates to improvements in equipment and methods for diagnostic purposes and has particular reference to the use of neutrons for the diagnosis of spatial and temporal information on the flow of hydrocarbons through gas turbine engines oil and fuel passages, internal combustion engines, hydraulic pumps and other dynamic fluid transfer system components.

It is known that fluids whose chemistry includes hydrogen radicals have a high capture cross-section for neutrons in the cold energy ranges. Furthermore, it is separately known that if the metal structures are placed in the path of a beam of neutrons then radiographic plates may be produced having good contrast so that the internal arrangement of the structure may be discerned. It has long been a problem in the art of gas turbine engines to determine information about the flow and priming characteristics of engines and their associated fuel and oil systems and to determine information about the extent of leakages through oil seals. These two pieces of information are particularly required during the development of engines and during in-service running for condition monitoring to establish the need or otherwise for overhaul. Hitherto the above information, if determinable at all, has only been available by extensive dismantling of the engine. Such dismantling is, of course, costly and is generally better avoided if possible. The present invention seeks to provide diagnostic apparatus and a method of diagnosis which will enable the above-mentioned disadvantages to be substantially avoided.

According to the present invention there is provided diagnostic equipment capable of determining information about temporal variations in the spatial distribution of fluids or components within apparatus, the fluids or components containing substances which are radicals of the element hydrogen, or other elements having relatively high mass attenuation coefficients for low energy neutrons, the diagnostic equipment comprising support means for positioning the apparatus in the path of a beam of neutron of energy less than 0.025 eV and of flux greater than $1\times10^3$ neutrons/sq. centimeter/second there being a neutron sensitive screen arranged to receive the neutrons emerging from the apparatus to produce on the screen an image representative of said temporally varying spatial distribution, there being further provided an image intensifying system for intensifying the image, to a visible image, said intensifier being adapted to be responsive to light levels of less than $10^{-6}$ foot Lambert and recording means for recording temporal variations in said visible image.

Also according to the present invention there is provided a method of diagnosis of information about the temporal variations in the spatial distribution of fluids or components within apparatus, the fluids or components containing substances which are radicals of the element hydrogen, or other elements having relatively high mass attenuation coefficients for low energy neutrons, the method comprising the steps of directing a beam of neutrons of energies less than 0.025 eV and of flux greater than $1\times10^3$ neutrons per square centimeter per second through the apparatus, receiving the neutrons emerging from the apparatus on a screen to produce an image thereon representative of said spatial and temporal distribution and subsequently intensifying the image to a visible light image by an image intensifying system adjusted to be responsive to light levels of less than $10^{-6}$ foot Lambert.

Preferably the neutron flux is greater than $10^6$ neutrons/square centimeter/second and the image intensifying system is adjusted to be responsive to light levels of less than $10^{-7}$ foot Lambert.

The equipment and method are especially adapted for diagnosing events happening in apparatus comprising oil and fuel systems.

It has been found that certain conventional lubricating oils incorporate many radicals of hydrogen in their structure. Because of the relatively high mass attenuation coefficients for hydrogen the lubricating oils are readily visible as intense dark areas on the visible image. This is very advantageous for certain purposes such as the determination and diagnosis of leakage paths but is disadvantageous in other circumstances. The disadvantages are particularly significant when it is desired to observe the flow of lubricants around bearing structures or to observe cavitation effects in flow lines. For these observations the detail of the bearing structure or cavitation effects are obscured because of the intense darkness of the oil as seen on the visible image.

In one aspect of the method there is provided a way of overcoming the aforementioned disadvantages.

According to this aspect of the method there is substituted for at least a portion of the liquid normally used in the apparatus a liquid having similar mechanical properties but having different mass attenuation properties for the low energy neutrons whereby to improve the information available from the visible light image.

One liquid we believe to be suitable for substituting for conventional lubricants is known by the systematic name per fluorodocosane which has the chemical formula $C_{21}F_{44}$ and whih can be used either alone or mixed with tri(n-octyl) methane $C_{25}H_{25}$ and which have mass attenuation coefficients of 0.15 and 6.8 barns respectively for cold neutrons. Alternatively deuterated oils are expected to give good results although their high relative cost makes them less desirable.

The diagnosis may be made whilst the apparatus is in operation, or alternatively it may be made whilst the apparatus is being driven from an external power supply.

Unfortunately, there currently exists no mobile prolific source of cold neutrons; therefore, it is necessary to arrange for diagnoses of apparatus to be carried out by moving the apparatus adjacent to a suitable fixed source of cold neutrons.

We have experimented with a nuclear reactor as a suitable source of cold neutrons. The reactor is provided with a window through which neutrons taking part in the fissile process within the reactor are extracted and subsequently passed through moderating and cooling substances such as Boron or Graphite followed by liquid hydrogen, to sequentially reduce their energies to lie within the range of thermal energies less than 0.025 eV, and preferably within the cold neutron energies (less than 0.005 eV). The beam is subsequently focussed using a focussing device made from Beryllium in known manner. It is believed certain mobile sources of cold neutrons will be commercially available in the future and are likely to be based around one of the following devices:

(a) A linear accelerator in which a beam of electrons is accelerated to the MeV energy ranges and subsequently utilised to bombard a target in which Beryllium is bonded to tungsten. X-radiation is generated by impingement of the electrons on the tungsten and nuclear processes within the Beryllium convert some of this x-radiation into neutrons. The neutron beam which is still contaminated with high energy x-radiation is subsequently passed through an oil tank to attenuate the x-radiation, and to moderate the neutron beam to thermal energies. The thermal neutrons are subsequently cooled to cold neutron energies using cooling techniques involving the use of liquid hydrogen which are well known per se. The energy conversion of electrons to neutrons is most efficient with this sort of apparatus, at energy levels around 8 MeV. At energy levels above 12 MeV the energy conversion produces a significantly lower yield. However, it is possible to make use of higher energy level linear accelerators operating above 12 MeV in an alternative way.

(b) With electron energy levels of the order of 12–15 MeV and intensity in the range 6–10,000 rads per minute at a meter, such as is achievable with a Linatron 6000 (Registered Trade Mark), a deuterium tritium reaction can be utilised to generate a high intensity neutron beam. This reaction can be further boosted by way of a uranium booster.

(c) The deuterium tritium reaction can also be initiated to generate high intensity neutron radiation by means of a Van der Graaf generator used as a proton accelerator.

(d) Alternatively, a device known as an insulated core transformer (ICT) is available which could be adapted to produce a beam of fast neutrons of high intensity. It is necessary to subsequently moderate the energy of these neutrons.

Other potential prolific sources of neutrons are also understood to be under active development for use with various non destructive testing techniques and it is probable that these sources could also be adapted to provide sources of cold neutrons.

We have found that it is possible to image lubrication oil and fuel flows taking place at the heart of a gas turbine engine through several inches of steel-equivalent thickness casings by utilizing cold neutron beams in the energy ranges and intensities as previously stated. The picture quality deteriorates as the energy of the neutrons increases beyond a certain level but this level is in practice ill-defined although it can generally be said that thermal neutron energies i.e. above 0.025 eV will yield relatively poorer results. It is necessary to do certain experiments to match the energy and flux of the neutron beam to the metal path thickness of the engine of the part of the engine being diagnosed. During priming tests for engine oilways and fuel systems it proved possible to render visible the moving boundaries of metals and fluids and to readily distinguish between the liquid and vapor phases.

The quality of the image produced on the output screen of the image intensifier is found to be improved when the source size of the neutrons decreases and, whilst a beam of neutrons is not strongly divergent (as is, for example, a beam of x-ray photons), nevertheless, image unsharpness is produced due to scattering of the neutrons by the first metal surface they encounter. Despite this unsharpness which is to a large extent unavoidable, we have found useful results can be readily achieved providing the metal path thicknesses traversed by the neutrons does not exceed about four inches of steel equivalent thickness.

An embodiment of the invention will now be described by way of example only and with reference to the accompanying drawings, in which:

FIG. 1 is a perspective view of an apparatus suitable for making diagnoses of gas turbine engine powerplants, FIG. 2 is a section through a part of the gas turbine engine of FIG. 1, FIG. 3 is a representation of an image as seen on the output screen of an image intensifier of the part of the gas turbine engine shown in FIG. 2, FIG. 4 is a representative view of a fuel system showing the boundary between liquid and vapor phases.

Figure 1:
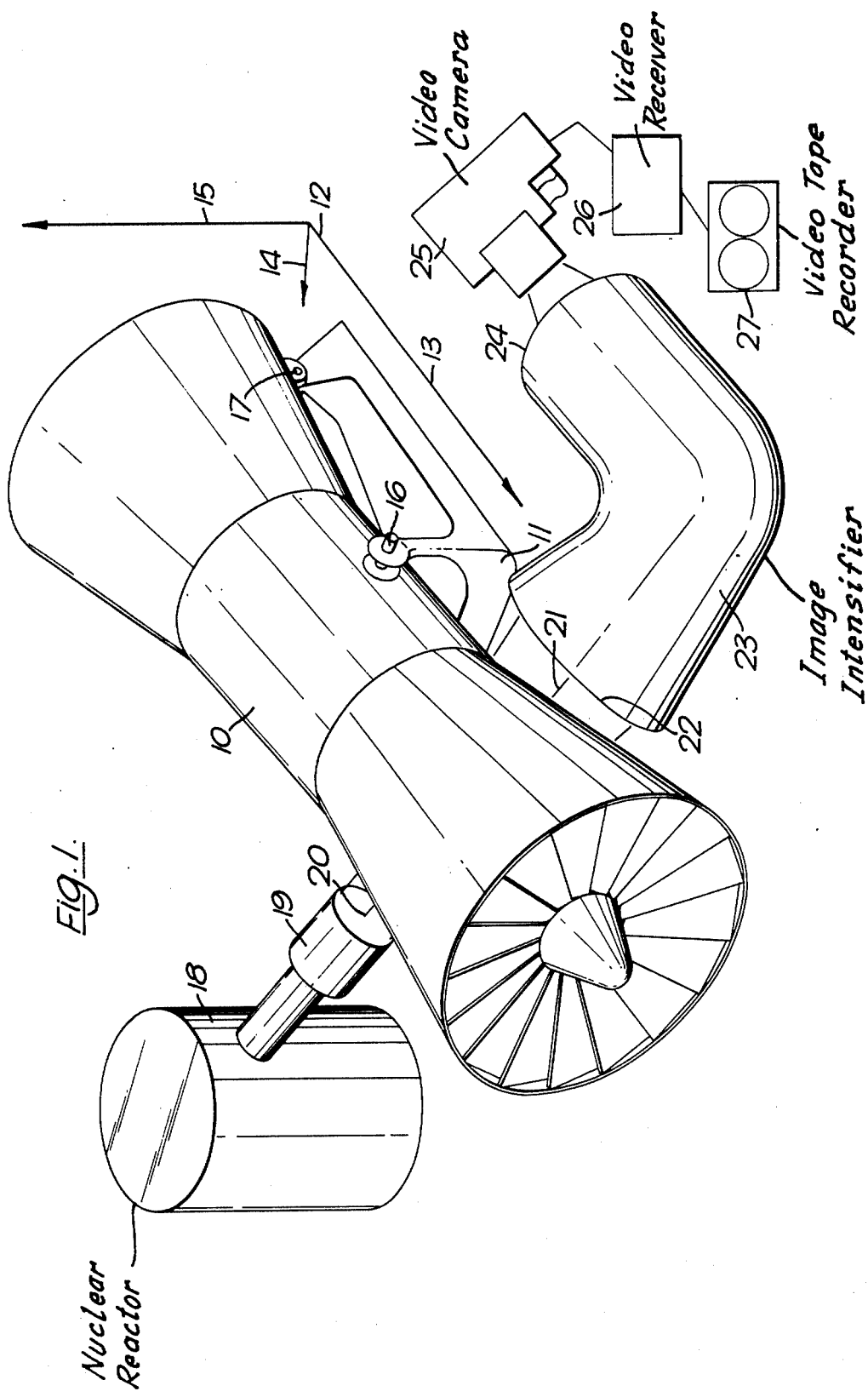

Referring now to FIG. 1 there is shown schematically a gas turbine engine 10 supported on a carriage 11 and movable on a supporting framework 12 in three co-ordinate directions 13, 14, 15. The carriage 11 supports the engine at its normal mounting points 16, 17 and the design of the carriage and framework is such that the engine can be operated up to full power conditions.

The engine is disposed adjacent a nuclear reactor 18 which is adapted in known manner to produce a beam of thermal neutrons which are subsequently cooled by a liquid hydrogen cooler 19 (known per se) to cold neutron energies i.e. less than 0.005 eV. The beam 20 of cold neutrons having a neutron flux of $1 \times 10^4$ neutrons/sq. centimeter/second is directed at the gas turbine engine 10 and is preferably absorbed by fluids or components within the gas turbine engine which include substances containing radicals of the element hydrogen. The beam 21 leaving the gas turbine engine is received on the input screen 22 of an image intensifier 23 which is set to be responsive to light levels below $10^{-7}$ foot Lambert.

The image intensifier is an Oulde Delft Delcalix (Regd. Trademark) X-ray image intensifier fitted with an input screen of Terbium activated Gadolinium Oxysulphide mounted on a reactor grade aluminum base. The intensifier is positioned in an insulated box (not shown) to protect it from any acoustic and seismic vibrations which may occur during running of the engine.

The image formed on the input screen 22 is representative of the distribution of hydrogenous matter within the gas turbine engine and, after intensification, allows the flow, and drain paths of lubricating or fuels oils to be visualized during running of the engine. The presence of air bubbles and the movement of the oil front is made visible and this is of particular use for investigating the priming of apparatus. The image formed on the input screen 22 is intensified in the image intensifier and the intensified image formed on the output screen 24 of the image intensifier is viewed by a low light level video camera 25. The visible image recorded by video camera 25 is displayed on a video receiver 26 and a video tape recorder 27 for forming a permanent record of the image on the input screen 24. Providing a sufficiently intense neutron source, i.e. one having a neutron flux in excess of $1 \times 10^4$ neutrons/sq. centimeter/second, is available to give a sufficiently intense image, then changes in the hydrogeneous distribution within the engine taking place faster than the scanning rate of the video camera can be recorded by replacing the video camera with a high speed cine camera. By hydrogenous distribution will be understood the distribution of substances containing radicals of the element hydrogen.

Certain components within the gas turbine engine, such as oil seals, wiring harnesses and pipe clips are made from hydrogenous material and these components also strongly absorb the cold neutron particles and show up as black areas on the output screen of the image intensifier. The image produced on the output screen of the image intensifier is a super-position of all the hydrogenous neutron absorbing matter throughout the section of the engine being observed and as such requires careful evaluation to establish the precise sequence of events being observed. By adjusting the position and/or orientation of the carriage 11 relative to the nuclear reactor 18, different sections of the engine can be observed as desired.

In order to clarify difficulties arising from the super-position of hydrogeneous matter particularly due for example to oil galleries positioned one behind the other we have found it useful to adopt the techniques of Stereoscopy. These are utilized by taking a pair of neutron radiographs corresponding to two orientations of the engine typically set at 5° on either side of a mean axial orientation. Markers of cadmium are attached to the engine and their known spatial positions serve to define a three dimensional coordinate framework which enables positional information about the hydrogenous distribution to be deduced. Alternatively qualitiative assessments can be made by fusing stereo pairs together in a stereo viewer.

Figure 2:
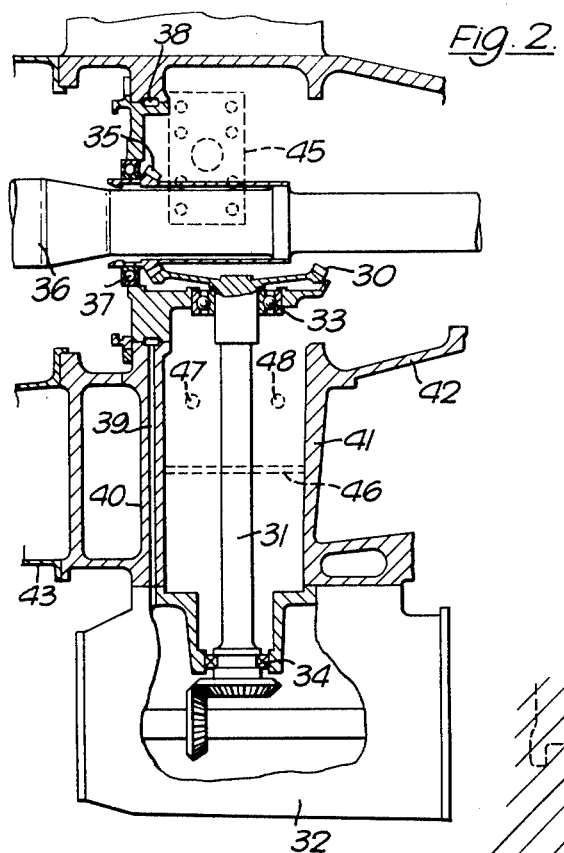
Figure 3:
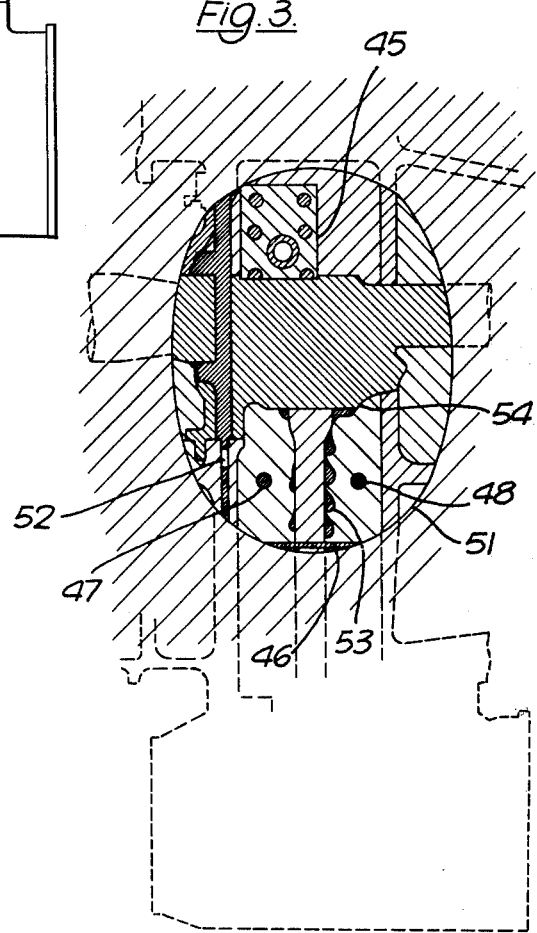

Turning now to FIGS. 2 and 3 there is shown a representation of the output image from the video camera compared with a drawing of the section of the engine through which it was taken. In the drawing (FIG. 2) can be seen the bevel gear 30 for driving the accessory drive shaft 31 of gas turbine engine gearbox 32. The bevel gear and shaft are supported on a ball bearing 33 and roller bearing 34 and driven from a mating gear 35 situated on the mainshaft 36 of the engine. The gear 35 and mainshaft are supported by a ball bearing 37 and all the bearings and gears are supplied with lubricating oil from an annular distribution gallery 38 provided in the support structure for the ball bearing 37. The distribution gallery 38 is itself supplied with oil from the accessory gearbox oil pump via an oilway 39 provided along the leading edge 40 of a vane 41 which supports the centerbody 42 of the engine from the engine outer casing 43. Shown in dotted lines on the drawing are the front engine mounting plates 45 one of which is provided on each side of the engine casing and a portion of the engine electrical wiring harness 46 and two plastic liners 47, 48 for pipe clips which secure a pipe to the engine casing.

In FIG. 3 an oval frame 51 borders the portion of the engine seen as a visible image on the output screen 24. In FIG. 3 the pitch of the various shading lines is seen to be representative of the radiograhic density on the output screen 24. Hydrogenous matter such as lubricating oil shows up as heavy black areas and areas of low neutron absorbancy show up as widely pitched shading lines. Thus the oilway 39, the annular gallery 38 and the bearing show up as intense black lines because of the oil within them whilst a break 52 in oilway 39 shows the passage of an air bubble through the oil system. Drops of oil 53 can be seen draining from the underside 54 of the bevel gear 30. Also readily visible in the picture are a portion of the wiring harness 46, the two plastic liners 47, 48 and the engine mounting plates 45.

During observation of the priming process it was possible to observe the progress of the oilfront through the oilway 39 and around the distribution gallery 38 and subsequently to observe the return flow of drain oil down the drive shaft 31. Certain areas of the image do not show any significant detail because the total steel equivalent thickness being penetrated by the neutron beam is approaching a limiting value of approximately 4".

Figure 4:
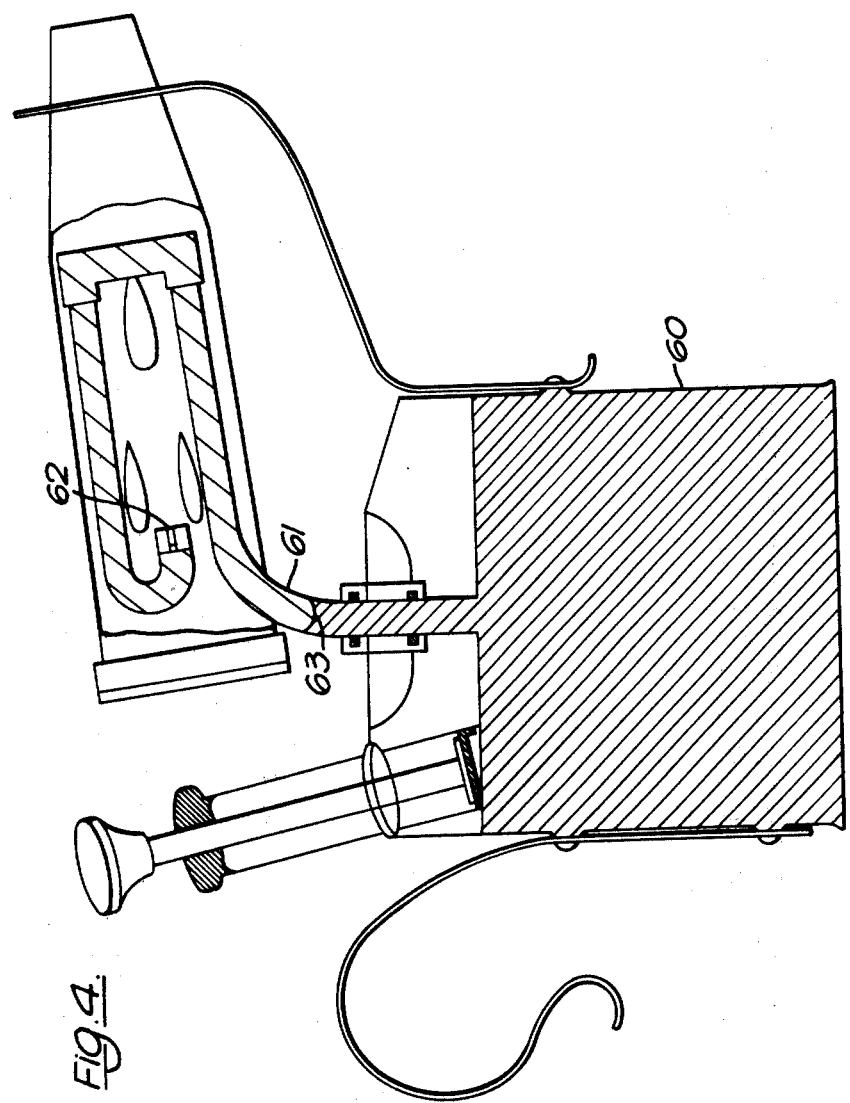

The application of the technique is not restricted to apparatus such as gas turbine engines but may also with advantage be used on other dynamic fluid transfer system components e.g. the blow-lamp, a representative image of which is shown in FIG. 4.

In FIG. 4 the generally cylindrical body 60 of the blow-lamp is shown three-quarters full of paraffin (a hydrogenous material) and the vaporizer tube 61 leading to the nozzle 62 can be seen to contain fluid to a level 63 and vapor beyond the level. The experiment was carried out with a 1" thick piece of steel plate interposed between the neutron source and the image intensifier. The experiment revealed the, to us, hitherto unknown phenomena that the level 63 oscillates at high frequency up and down the vaporizer tube 61 during the operation of the blow-lamp.

Figure 5:
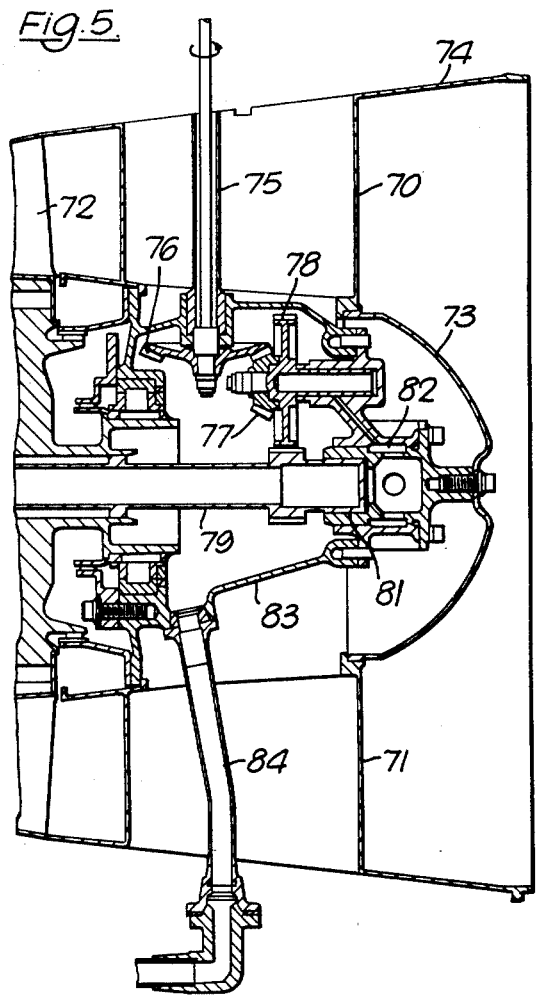
FIG. 5 is a section though the rear end of a gas turbine engine.
Figure 6:
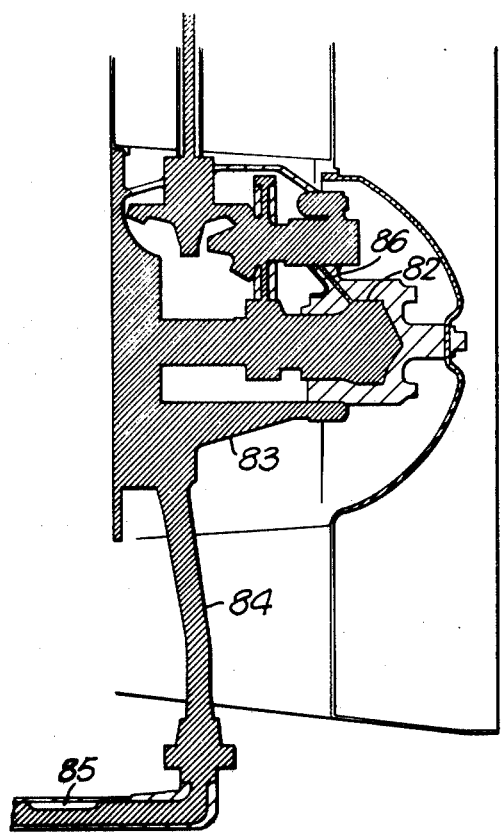
FIG. 6 is a representation of the equivalent portion of the gas turbine engine of FIG. 5 as viewed on the output screen of an image intensifier system and produced by irradiating the engine with neutrons.
Figure 7:
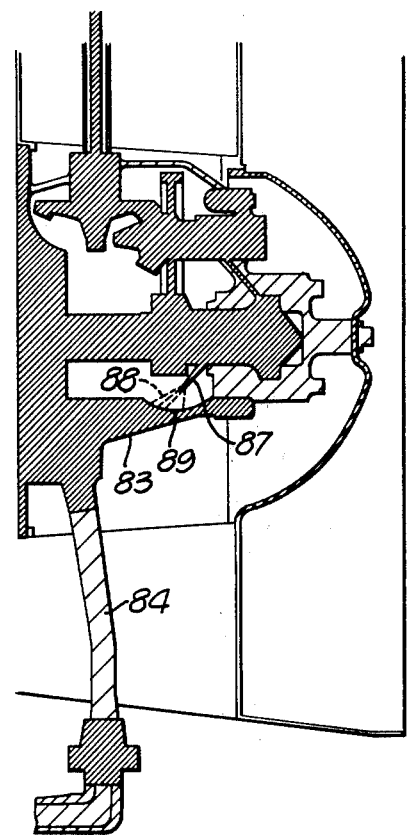
FIG. 7 is a similar representation to that of FIG. 6 but taken with the engine running at full power.

Referring now to FIGS. 5, 6, 7 there can be seen representations of the best results we have so far obtained by neutron irradiation of a gas turbine engine. In FIG. 5 there is identified two vanes 70, 71 downstream of the turbine 72 which locate the exhaust center body 73 of the engine from the casing 74. Housed within the vane 70 is an accessory drive shaft 75 carrying at its inner end a bevel gear 76 which mates with a second bevel gear 77 connected for rotation with a lay gear 78 which is in turn driven from the main shaft 79 of the engine.

The rear end of the main shaft is supported in a plain bearing 81 lubricated by pressurized oil from a chamber 82.

Oil escaping from the bearing is collected in a depression 83 from which it is drained by a scavenge pump (not shown) via the scavenge tube 84.

Turning now to FIG. 6 there is shown a representation of the video image obtained by irradiating the engine with a neutron flux of $10^6$ neutrons/square centimeter/second from a nuclear reactor. As before the neutron radiation ranges from the cold neutron energies up to thermal energies with an upper limit of 0.025 eV. The precise experimental arrangement is similar to that described in relation to FIGS. 1, 2 and 3, and as before the pitch of the shaded lines is proportional to the intensity of the radiographic image.

In FIG. 6 for which the engine was shut down it will be seen that the chamber 82 depression 83 and scavenge tube 84 are full of oil except for the presence of an air bubble 85. Similarly oilway 86 which carries lubricant to the lay gear 78 is primed with oil.

When the engine was started and accelerated up to its full power setting the picture could be observed changing until the steady state picture presented in FIG. 7 was obtained. From FIG. 7 it can be seen a jet of oil 87 issuing from the plain bearing 81 and splitting up into a spray of oil mist 88. The oil mist impinges on the surface of the oil collected in the depression 83 and produces a concave depression 89 in the oil. During this experiment we were surprised to discover an anomaly in the functioning of the oil scavenge system due to the degree of aeration of the oil passing through the scavenge tube 84.

In producing images of moving fluids by neutron beams a problem arises when it is desired to observe the flow of lubricating oils around bearing structures or aspects of cavitation in fuel or oil fluid transfer systems. The problem arises because the hydrocarbon, lubrication or fuel oils contain a sufficient number of radicals of the element hydrogen to strongly attenuate the neutron beam and give rise to an intense dark image on the imaging system. This problem is overcome by substituting for at least a portion of the fuel or lubricating oil a liquid having similar mechanical properties but containing fewer hydrogen radicals. This then renders the liquid partially transparent to the neutrons and allows the underlying structures or cavitation patterns to be observed.

One liquid we believe to be suitable for substituting for conventional lubricants is known by the systematic name per fluorodocosane which has the chemical formula $C_{21} F_{44}$ and which can be used either alone or mixed with tri (n-octyl) methane $C_{25} H_{52}$ and which have mass attenuation coefficients of 0.15 and 6.8 barns respectively for cold neutrons. Alternatively deuterated oils are expected to give good results although their high relative cost makes them less desirable. Whilst the above described experiments have been carried out using neutron fluxes in excess of $10^4$ neutrons/sq. centimeter/second and an image intensifier set to be responsive to light levels below $10^{-7}$ foot Lambert, it is possible for certain less radiographically dense apparatus to use a neutron flux of $1 \times 10^3$ neturons/sq. centimeter/second and an intensifier responsive to light levels below $10^{-6}$ foot Lambert.

Whilst hydrogenous matter is the most readily visible because of its relatively high mass attenuation coefficient certain other elements, principally Boron and Cadmium, also have relatively high mass attenuation coefficients. Thus, diagnoses can readily be made of the spatial distribtution of substances containing radicals of the elements Boron and Cadmium.

We have also carried out experiments using apparatus such as dynamic fuel transfer systems, in particular a gas turbine engine fuel pump, and have found it possible to diagnose occurrences within the pump not hitherto suspected. One especial feature to be revealed was the order of filling of certain chambers within the fuel pump which was contrary to that expected by the designers responsible for the pump. It will be appreciated that the availability of this sort of information made possible by the above described techniques enables significant design modifications leading to improved efficiency to be made, in particular use of the techniques herein described should find particular use in investigating the lubrication of internal combustion engines.

I claim:

1. Diagnostic equipment for providing information relating to the movement of a radiograhically distinct substance within an apparatus, said substance having a mass attenuation coefficient for neutrons with an energy less than 0.025 eV which is low with respect to that of the components of said apparatus surrounding said substance, said equipment comprising neutron generating means for generating a beam of neutrons having energies less than 0.025 eV and a flux greater than $10^3$ neutrons per square centimeter per second, support means for positioning said apparatus in the path of said neutron beam, a neutron sensitive screen for receiving the neutrons emerging from said apparatus, a visible image being produced on said screen which is representative of the neutrons absorbed within said apparatus, said image changing directly in correspondence with said movement, an image intensifying system responsive to light levels of less than $10^{-6}$ foot Lambert, and recording means for recording said visible image.

2. A method of obtaining information relating to the movement of a radiographically distinct substance within an apparatus comprising placing said radiographically distinct substance within said apparatus, said substance having a mass attenuation coefficient for neutrons with an energy less than 0.025 eV which is low with respect to that of the components of said apparatus surrounding said substance, transmitting a beam of neutrons having energies less than 0.025 eV and a flux greater than $10^3$ neutrons per square centimeter per second through said apparatus, receiving the neutrons emerging from said apparatus on a neutron sensitive screen to produce on said screen an image representative of the neutrons absorbed within said apparatus, said image changing directly in correspondence with said movement, and intensifying said image to produce a visible light image by an image intensifying system responsive to light levels of less than $10^{-6}$ foot Lamberts.

3. A method according to claim 2 wherein said neutron flux is greater than $10^6$ neutrons per square centimeter per second.

4. A method according to claim 2 wherein said image intensifying system is responsive to light levels of less than $10^{-7}$ foot Lambert.

5. A method according to claim 3 wherein said image intensifying system is responsive to light levels of less than $10^{-7}$ foot Lambert.

6. A method according to claim 2 wherein said substance is a hydrocarbon liquid, at least a portion thereof having a relatively low mass attenuation coefficient for low energy neutrons.

7. A method according to claim 6 wherein the portion of said hydrocarbon liquid having a relatively low mass attenuation coefficient for low energy neutrons comprises per fluorodocosane.

8. A method according to claim 6 wherein the portion of said hydrocarbon liquid having a relatively low mass attenuation coefficient for low energy neutrons comprises a deuterated hydrocarbon.

9. A method according to claim 3 wherein said substance is a hydrocarbon liquid, at least a portion thereof having a relatively low mass attenuation coefficient for low energy neutrons.

10. A method according to claim 4 wherein said substance is a hydrocarbon liquid, at least a portion thereof having a relatively low mass attenuation coefficient for low energy neutrons.

* * * * *

Disclaimer 4,152,598.—*Peter A. E. Stewart*, Bristol, England. LUBRICANT DISTRIBUTION DETERMINATION BY NEUTRON RADIOGRAPHY. Patent dated May 1, 1979. Disclaimer filed Jan. 18, 1985, by the assignee, *Rolls-Royce (1971) Ltd.*

Hereby enters this disclaimer to all claims of said patent.
[*Official Gazette March 12, 1985.*]